United States Patent
Friend et al.

(10) Patent No.: US 8,753,811 B2
(45) Date of Patent: *Jun. 17, 2014

(54) METHOD FOR MAKING POPULATIONS OF DEFINED NUCLEIC ACID MOLECULES

(75) Inventors: Stephen H. Friend, Seattle, WA (US); Michele A. Cleary, Jamison, PA (US); Ernest M. Coffey, Shoreline, WA (US); Kristopher A. Killian, Savoy, IL (US); Gregory J. Hannon, Huntington, NY (US); Patrick Paddison, Seattle, WA (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/398,560

(22) Filed: Feb. 16, 2012

(65) Prior Publication Data
US 2012/0149602 A1    Jun. 14, 2012

Related U.S. Application Data

(63) Continuation of application No. 10/860,559, filed on Jun. 2, 2004, now Pat. No. 8,133,670.

(60) Provisional application No. 60/478,382, filed on Jun. 13, 2003.

(51) Int. Cl.
*C12Q 1/68*    (2006.01)
*C12P 19/34*    (2006.01)
*C07H 21/02*    (2006.01)
*C07H 21/04*    (2006.01)

(52) U.S. Cl.
USPC .......... 435/6.1; 435/91.2; 536/23.1; 536/24.3

(58) Field of Classification Search
None
See application file for complete search history.

(56) References Cited

U.S. PATENT DOCUMENTS

| 5,143,854 A | 9/1992 | Pirrung et al. |
| 5,384,261 A | 1/1995 | Winkler et al. |
| 5,474,796 A | 12/1995 | Brennan |
| 5,677,195 A | 10/1997 | Winkler et al. |

(Continued)

FOREIGN PATENT DOCUMENTS

| WO | WO-90/15070 | 12/1990 |
| WO | WO-92/10092 | 6/1992 |

(Continued)

OTHER PUBLICATIONS

Needels, M.C., et al., "Generation and screening of an oligonucleotide-encoded synthetic peptide library", PNAS USA, Nov. 1993, vol. 90, pp. 10700-10704.

(Continued)

*Primary Examiner* — Teresa E Strzelecka
(74) *Attorney, Agent, or Firm* — Wilmer Cutler Pickering Hale and Dorr LLP (57) ABSTRACT

The present invention provides methods of making a population of nucleic acid molecules, wherein each nucleic acid molecule comprises a predetermined nucleic acid sequence, each of said methods comprising the steps of: (a) synthesizing, on a substrate, a population of nucleic acid molecules wherein: i) each synthesized nucleic acid molecule comprises a predetermined nucleic acid sequence; and ii) each synthesized nucleic acid molecule is localized to a defined area of said substrate; (b) harvesting said population of synthesized nucleic acid molecules from said substrate to yield harvested nucleic acid molecules; and (c) introducing said harvested nucleic acid molecules into vector molecules.

24 Claims, 1 Drawing Sheet

(56) References Cited

U.S. PATENT DOCUMENTS

| | | | |
|---|---|---|---|
| 5,763,175 | A | 6/1998 | Brenner |
| 5,843,655 | A | 12/1998 | McGall |
| 6,028,189 | A | 2/2000 | Blanchard |
| 6,271,002 | B1 | 8/2001 | Linsley |
| 6,280,950 | B1 | 8/2001 | Lipshutz et al. |
| 6,419,883 | B1 | 7/2002 | Blanchard |
| 6,440,677 | B2 | 8/2002 | Lipshutz et al. |
| 6,586,211 | B1 | 7/2003 | Stahler et al. |
| 7,604,996 | B1 | 10/2009 | Stuelpnagel et al. |
| 2002/0045169 | A1 | 4/2002 | Shoemaker et al. |
| 2003/0068643 | A1 | 4/2003 | Brennan et al. |
| 2004/0132029 | A1 | 7/2004 | Sussman et al. |

FOREIGN PATENT DOCUMENTS

| | | |
|---|---|---|
| WO | WO-93/09668 | 5/1993 |
| WO | WO-00/13018 | 3/2000 |
| WO | WO-00/49142 | 8/2000 |
| WO | WO-2004/039953 | 5/2004 |

OTHER PUBLICATIONS

Bonaldo, M. F., et al., "Normalization and subtraction: two approaches to facilitate gene discovery", Genome Research, 1996, vol. 6, pp. 791-806.

Lambert, Kris N., et al., "cDNA Library Construction Using Streptavidin-Paramagnetic Beads and PCR", Nucleic Acid Protocols Handbook, 2000, pp. 289-294.

Roeder, Thomas, "Solid-phase cDNA library construction, a versatile approach", Nucleic Acids Research, 1998, vol. 26, No. 14, pp. 3451-3452.

Cleary, M.A., et al., "Production of Complex Nucleic Acid Libraries Using Highly Parallel in Situ Oligonucleotide Synthesis", Nature Methods, Dec. 2004, vol. 1, No. 3, pp. 241-248.

Leproust, E., et al., "Characterization of Oligodeoxyribonucleotide Synthesis on Glass Plates", Nucleic Acids Research, Mar. 2001, vol. 29, No. 10, pp. 2171-2180.

Tabor, Stanley, et al., "A bacteriophage T7 RNA polymerase/promoter system for controlled exclusive expression of specific genes", PNAS USA, Feb. 1985, vol. 82, pp. 1074-1078.

Matthes, H.W.D., et al., "Simultaneous Rapid Chemical Synthesis of Over One Hundred Oligonucleotides on a Microscale", EMBO J., 1984, vol. 3, No. 4, pp. 801-805.

McGall, G.H., et al., "The Efficiency of Light-Directed Synthesis of DNA Arrays on Glass Substrates", JACS, Jun. 4, 1997, vol. 119, No. 22, pp. 5081-5090.

Pirrung, M.C., et al., "Comparison of Methods for Photochemical Phosphoramidite-Based DNA Synthesis", J. Org. Chem., May 1995, vol. 60, pp. 6270-6276.

Rayner, S., et al., "MerMade: An Oligodeoxyribonucleotide Synthesizer for High Throughput Oligonucleotide Production in Dual 96-Well Plates", Genome Res., 1998, pp. 741-747.

Singh-Gasson, S., et al., "Maskless Fabrication of Light-Directed Oligonucleotide Microarrays Using a Digital Micromirror Array", Nat. Biotechnol., Oct. 1999, vol. 17, pp. 974-978.

Blanchard, A., "Synthetic DNA Arrays", Genetic Engineering, 1998, vol. 20, pp. 111-123.

Blanchard, A.P., et al., "High-Density Oligonucleotide Arrays", Biosensors and Bioelectronics, 1996, vol. 11, pp. 687-690.

Froehler, B.C., et al., "Synthesis of DNA Via Deoxynucleoside H-Phosphonate Intermediates", Nucleic Acids Res., 1986, vol. 14, pp. 5399-5407.

Gait, M.J., Oligonucleotide Synthesis: A Practical Approach, IRL Press, Oxford University Press, 1984, 119 pages.

Guatelli, J.C., et al., "Isothermal, in Vitro Amplications of Nucleic Acids by a Multienzyme Reaction Modeled After Retroviral Replication", PNAS, 1990, vol. 87, pp. 1874-1878.

Halliwell, C.M., et al., "A Factorial Analysis of Silanization Conditions for the Immobilization of Oligonucleotides on Glass Surfaces", Anal. Chem., 2001, vol. 73, pp. 2476-2483.

Hughes, T.R., et al., "Expression Profiling Using Microarrays Fabricated by an Ink-Jet Oligonucleotide Synthesizer", Nat. Biotechnol., Apr. 2001, vol. 19, pp. 342-347.

Kyser, E.L., et al., "Design of an Impulse Ink Jet", J. Appl. Photographic Eng., 1981, vol. 7, pp. 73-79.

Landegren, U., et al., "A Ligase-Mediated Gene Detection Technique", Science, 1988, vol. 241, pp. 1077-1080.

Lipshutz, R.J., et al., "High Density Synthetic Oligonucleotide Arrays", Nat. Genet., 1999, vol. 21, pp. 20-24.

Lockhart, D.J., et al., "Expression Monitoring by Hybridization to High-Density Oligonucleotide Arrays", Nat. Biotechnol., 1996, vol. 14, pp. 1675-1680.

Maskos, U., et al., "Oligonucleotide Hybridisations on Glass Supports: A Novel Linker for Oligonucleotide Synthesis and Hybridization Properties of Oligonucleotide Synthesized In Situ", Nucl. Acids Res., 1992, vol. 20., No. 7, pp. 1679-1684.

McBride, L.J., et al., "An Investigation of Several Deoxynucleoside Phosphoramidites Useful for Synthesizing Deoxyoligonucleotides", Tetrahedron Letters, 1983, vol. 24, pp. 245-248.

McGall, G., et al., "Light-Directed Synthesis of High-Density Oligonucleotide Arrays Using Semiconductor Photoresists", PNAS USA, 1996, vol. 93, pp. 13555-13560.

Olejnik, J., et al., "Photocleavable Affinity Tags for Isolation and Detection of Biomolecules", Methods Enzymol., 1998, vol. 291, pp. 135-154.

Pease, A.C., et al., "Light-Generated Oligonucleotide Arrays for Rapid DNA Sequence Analysis", PNAS, 1994, vol. 91, pp. 5022-5026.

Schena, M., "Genome Analysis with Gene Expression Microarrays", Bioessays, 1996, vol. 18, No. 5, pp. 427-431.

Scott, S., et al., "A Universal Support for Oligonucleotide Synthesis", Innovations and Perspectives in Solid Phase Synthesis, 3rd International Symposium, Roger Epton ed., Mayflower Worldwide, 1994, pp. 115-124.

Shoemaker, D.D., et al., "Experimental Annotation of the Human Genome Using Microarray Technology", Nature, 2001, vol. 409, pp. 922-927.

Silberzan, P., et al., "Silanation of Silica Surfaces. A New Method of Constructing Pure or Mixed Monolayers", Langmuir, 1991, vol. 7, pp. 1647-1651.

Wu, D.Y., et al., "The Ligation Amplication Reaction (LAR)-Amplication of Specific DNA Sequences Using Sequential Rounds of Template-Dependent Ligation", Genomics, 1989, vol. 4, pp. 560-569.

METHOD FOR MAKING POPULATIONS OF DEFINED NUCLEIC ACID MOLECULES

CROSS-REFERENCE TO RELATED APPLICATIONS

This application is a continuation of U.S. Ser. No. 10/860,559, filed on Jun. 2, 2004, which claims the benefit of Provisional Application No. 60/478,382, filed Jun. 13, 2003. The entire teachings of each of the above-referenced applications are incorporated herein by reference.

FIELD OF THE INVENTION

The present invention relates generally to the field of genomic analysis, and more particularly to methods for making libraries comprising a population of predetermined nucleic acid sequences.

BACKGROUND OF THE INVENTION

There are many applications for populations of nucleic acid molecules (referred to in the art as nucleic acid libraries) wherein the sequence of each nucleic acid molecule within the library is predetermined and known. Such libraries are useful, for example, in any situation in which it is desired to mix numerous sequences that differ from one another at one or more defined regions. For example, an expression library can be made in which each nucleic acid encodes a different amino acid chain variant corresponding to a specific peptide. The library of expressed protein fragments can then be screened by a variety of techniques, (e.g., antibody recognition, small molecule binding, nucleic acid binding, and protein-protein interaction) to identify peptide variants of interest.

Typically, such populations of mixed nucleic acids are constructed through the pooling of nucleic acid molecules that are synthesized individually. Such individual synthesis of nucleic acid molecules, however, is costly, inefficient, and labor intensive. Therefore, there is a need for improved methods for synthesizing populations of nucleic acid molecules wherein each nucleic acid molecule has a known, predetermined, sequence.

SUMMARY OF THE INVENTION

In accordance with the foregoing, in one aspect the present invention provides methods of making populations of nucleic acid molecules, wherein each nucleic acid molecule comprises a predetermined nucleic acid sequence, each of said methods comprising the steps of: (a) synthesizing a population of nucleic acid molecules on a substrate, wherein: i) each synthesized nucleic acid molecule comprises a predetermined nucleic acid sequence; and ii) each synthesized nucleic acid molecule is localized to a defined area of said substrate; (b) harvesting said population of synthesized nucleic acid molecules from said substrate to yield harvested nucleic acid molecules; and (c) introducing said harvested nucleic acid molecules into vector molecules. In some embodiments, the methods further comprise the step of amplifying the population of synthesized nucleic acid molecules, and/or harvested nucleic acid molecules, prior to introducing the harvested nucleic acid molecules into vector molecules.

In some embodiments, the synthesized nucleic acid molecules have a range in length of from 20 nucleotides to 200 nucleotides, or longer (e.g., from 30 nucleotides to 100 nucleotides, or from 60 nucleotides to 100 nucleotides, or from 80 nucleotides to 100 nucleotides, or from 100 nucleotides to 200 nucleotides, or greater than 200 nucleotides). In some embodiments, each of the synthesized nucleic acid molecules comprises a 5' primer binding region, a target sequence, and a 3' primer binding region, wherein the target sequence is located between the 5' primer binding region and the 3' primer binding region. In some embodiments, each of the synthesized nucleic acid molecules further comprises a target identifier sequence located anywhere within the synthesized nucleic acid molecule, such as immediately adjacent to either the 5' end or the 3' end of the nucleic acid molecule. In some embodiments, a particular defined area of the substrate contains synthesized nucleic acid molecules comprising nucleic acid sequences essentially identical to the nucleic acid sequence of every other synthesized nucleic acid molecule localized to the same defined area of the substrate. In some embodiments, the target sequence of each nucleic acid molecule localized to a particular defined area of the substrate is different from the target sequence(s) of each nucleic acid molecule localized to some, or all, of the other defined areas of the substrate. In some embodiments, the substrate comprises a multiplicity of defined areas wherein at least two separate defined areas contain nucleic acid molecules comprising essentially identical nucleic acid sequences, and wherein all of the nucleic acid molecules within a defined area have the same nucleic acid sequence.

In one embodiment, the population of nucleic acid molecules is synthesized on a glass substrate using an ink jet printer, and the nucleic acid molecules of the population of synthesized nucleic acid molecules have an average length of from about 80 to about 100 nucleotides.

The methods of the invention can be used to create populations of nucleic acid molecules (also referred to in the art as "libraries" of nucleic acid molecules) useful for a variety of purposes, such as, for example, antibody binding affinity libraries, phage display libraries, libraries for combinatorial peptide sequence generation, DNA binding site selection libraries, protein binding site selection libraries, promoter region analysis libraries, libraries for restriction enzyme recognition site analysis, short hairpin RNA (shRNA) expression libraries, small interfering RNA (siRNA) expression libraries, and libraries designed for the generation of chromosomal probes.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Unless specifically defined herein, all terms used herein have the same meaning as they would to one skilled in the art of the present invention. Practitioners are particularly directed to Sambrook et al. (1989) *Molecular Cloning: A Laboratory Manual*, 2$^{nd}$ ed., Cold Spring Harbor Press, Plainview, N.Y. (1989), and Ausubel et al., *Current Protocols in*

*Molecular Biology* (Supplement 47), John Wiley & Sons, New York (1999), for definitions and terms of the art.

In one aspect, the present invention provides methods of making a population of nucleic acid molecules, wherein each nucleic acid molecule comprises a predetermined nucleic acid sequence, each of said methods comprising the steps of: (a) synthesizing a population of nucleic acid molecules on a substrate, wherein i) each synthesized nucleic acid molecule comprises a predetermined nucleic acid sequence, and ii) each synthesized nucleic acid molecule is localized to a defined area of said substrate; (b) harvesting said population of synthesized nucleic acid molecules from said substrate to yield harvested nucleic acid molecules; and (c) introducing said harvested nucleic acid molecules into vector molecules.

As used herein, the term "nucleic acid molecule" encompasses both deoxyribonucleotides and ribonucleotides and refers to a polymeric form of nucleotides including two or more nucleotide monomers. The nucleotides can be naturally occurring, artificial and/or modified nucleotides. Examples of nucleic acid molecules include oligonucleotides that typically range in length from 2 nucleotides to about 100 nucleotides, and polynucleotides, which typically have a length greater than about 100 nucleotides.

As used herein, the phrase "predetermined nucleic acid sequence" means that the nucleic acid sequence of a nucleic acid molecule is known and was chosen before synthesis of the nucleic acid molecule in accordance with the invention disclosed herein. The methods of the present invention are thus distinguished, in at least one aspect, from prior art methods for making a population of nucleic acid molecules in which the sequences for some, or all, of the synthesized nucleic acid molecules (e.g., mRNA molecules, cDNA molecules) are completely unknown, or are only partially known (i.e., the sequences of part of each synthesized nucleic acid molecule are known).

As used herein, the term "essentially identical" as applied to synthesized nucleic acid molecules refers to nucleic acid molecules that are designed to have identical nucleic acid sequences, but that may occasionally contain minor sequence variations in comparison to a desired sequence due to base changes introduced during the nucleic acid molecule synthesis process, or due to other random processes. As used herein, essentially identical nucleic acid molecules are at least 95% identical to the desired sequence, such as at least 96%, such as at least 97%, such as at least 98%, such as at least 99% identical or absolutely identical, to the desired sequence.

As used herein, the term "complement" when used in connection with a nucleic acid molecule refers to the complementary nucleic acid sequence as determined by Watson-Crick base pairing. For example, the complement of the nucleic acid sequence 5'CCATG3' is 5'CATGG3'.

The methods of the invention are useful in any situation in which it is desirable to make populations of nucleic acid molecules wherein each nucleic acid molecule has a predetermined nucleic acid sequence. An art-recognized term for a population of nucleic acid molecules is a "library" of nucleic acid molecules. The term "library" is usually, although not necessarily, applied to populations of nucleic acid molecules that have been introduced into vector molecules that facilitate expression of the nucleic acid molecules to yield other nucleic acid molecules (e.g., RNA molecules) and/or proteins (or fragments of complete proteins). For example, the methods of the invention can be used to create nucleic acid libraries for antibody diversity studies, phage display, combinatorial peptide sequence generation, DNA binding site selection, promoter structural analysis, identification of regulatory sequences, restriction enzyme recognition site analysis, short hairpin RNA (shRNA) expression, small interfering RNA (siRNA) expression, chromosomal probe generation, genomic insertional mutagenesis, creation of nucleic acid multimers and screening sequences for protein domain solubility in expression systems.

By way of non-limiting example, the methods of the invention can be used to generate a nucleic acid library to analyze variations of a protein subdomain, such as, for example, a catalytic domain, activation domain, DNA-binding domain, protein interaction domain, nuclear localization domain, or antibody structural domain. The methods are also useful, for example, for generating libraries expressing random amino acid sequence polypeptide fragments, or for producing random mutagenesis of protein fragments. Such libraries can be designed in various ways so that either the insert alone is expressed, the insert is embedded into a framework of the wild-type, or engineered, protein flanking sequence residing in the vector such that variations of the protein are expressed, the insert is fused to a reporter protein, the insert is tagged with an epitope, or the insert itself can encode an epitope. Such libraries can be expressed, for example, intracellularly in tissue culture, in bacterial cells (e.g., as GST fusions), in animal model systems, in in vitro translation systems (e.g., rabbit reticulocyte lysate), in cell extracts and through phage display.

By way of non-limiting example, the methods of the invention can be used to generate a nucleic acid library to analyze the functional relationship between the amino acid sequence and binding specificity of a DNA-binding protein, such as, for example, a zinc finger protein. Zinc finger proteins contain DNA binding motifs (referred to as "fingers") which typically contain an approximately 30 amino acid, zinc chelating, DNA binding subdomain. (see e.g., Berg & Shi, *Science* 271:1081-1085 (1996)). The DNA binding affinity of zinc finger proteins can be enhanced through the design and synthesis of a preselected population of sequence variations of the DNA binding subdomain, such as a sequential substitution of each nucleic acid residue in the DNA binding subdomain. Once synthesized, the population of nucleic acid molecules containing sequence variations of the DNA binding motif can be cloned into a vector to form a library, which can be introduced into host cells and expressed therein. The polypeptides encoded by the library of predetermined nucleic acid molecules can then be screened for the desired properties, such as, for example, enhanced DNA binding affinity. In the case of a DNA binding protein whose recognition sequence is not known, the methods of the invention can be used to generate a nucleic acid library containing random sequences to enable selection of the sequence with the highest affinity for the DNA binding site. An example of such an approach is a yeast one-hybrid system, in which the fusion protein remains constant and the DNA recognition sequence driving expression of the reporter construct contains random sequences which are selected based on expression of the reporter gene.

Again by way of non-limiting example, the methods of the invention can be used to generate cassettes for genomic insertional mutagenesis. For example, synthesized nucleic acid molecules containing sequences homologous to a specific genomic locus can be cloned into a targeting construct to allow for homologous recombination and disruption of a specific genomic region.

By way of further example, the methods of the invention can be used to produce multimers of specific sequences. To produce such multimers, single stranded nucleic acid molecules are synthesized in accordance with the present invention, and then rendered double stranded (e.g., by annealing complementary single stranded nucleic acid molecules).

Individual, double-stranded, nucleic acid molecules can be joined using a DNA ligase. Multimers of a desired size can be selected prior to cloning.

In another exemplary use, the methods of the invention can be used for testing protein domain solubility in bacteria. This can be achieved, for example, by fusing the synthesized nucleic acid molecules to the coding region of green fluorescent protein (GFP) in a bacterial protein expression plasmid, and screening for fluorescence in bacteria.

By way of non-limiting example, the methods of the invention can be used to generate a library expressing variations of functional RNAs (e.g., short hairpin RNAs, short interfering RNAs, ribozymes, small nuclear RNAs, small nucleolar RNAs, transfer RNAs, small temporal RNAs, etc). Such libraries can be designed so that either the insert alone is expressed, the insert is embedded into a framework of wild-type RNA flanking sequence, or the insert is fused to a reporter gene (e.g., luciferase, GFP). Such libraries can be expressed, for example, in vitro, in bacterial cells, mammalian cells or in animal model systems.

Again by way of non-limiting example, the methods of the invention can be used to make a phage display library using a phage DNA vector from which is transcribed a fusion protein, a portion of which is encoded by an insert nucleic acid molecule introduced into the vector. Phage display libraries are useful, for example to isolate antibody fragments (e.g., Fab, Fv, scFv and VH) based on antibody specificity to a particular antigen. A phage containing an insert nucleic acid molecule undergoes replication and transcription in the cell to yield a fusion protein. The leader sequence of the fusion protein directs the transport of the fusion protein to the tip of the phage particle. Thus, the fusion protein which is partially encoded by the insert nucleic acid molecule is displayed on the phage particle for detection and selection.

By way of further example, the methods of the invention can be used to make a peptide display library. One exemplary peptide display method involves the presentation of a peptide sequence on the surface of a filamentous bacteriophage, typically as a fusion with a bacteriophage coat protein. The bacteriophage library can be incubated with an immobilized, predetermined macromolecule or small molecule (e.g., a receptor) so that bacteriophage particles which present a peptide sequence that binds to the immobilized macromolecule can be differentially partitioned from those that do not present peptide sequences that bind to the predetermined macromolecule. The bacteriophage particles that are bound to the immobilized macromolecule are then recovered and replicated to amplify the selected bacteriophage sub-population for a subsequent round of affinity enrichment and phage replication. After several rounds of affinity enrichment and phage replication, the bacteriophage library members that are thus selected are isolated and the nucleotide sequence encoding the displayed peptide sequence is determined, thereby identifying the sequence(s) of peptides that bind to the predetermined macromolecule (e.g., receptor). Such peptide display methods are further described, for example, in PCT Patent Application Nos. 91/17271, 91/18980, 91/19818 and 93/08278.

In the practice of the present invention, nucleic acid molecules are synthesized on a surface of a substrate, typically a flat substrate, which may be textured or treated to increase surface area. The surface of the substrate typically has, or is chemically modified to have, reactive groups suitable for attaching organic molecules. Examples of such substrates include, but are not limited to, glass, silica, silicon, plastic, (e.g., polypropylene, polystyrene, Teflon™, polyethylimine, nylon, polyester), polyacrylamide, fiberglass, nitrocellulose, cellulose acetate, or other suitable materials. In some embodiments, glass is the preferred substrate. The substrate may be treated in such a way as to enhance the attachment of nucleic acid molecules. For example, a glass substrate may be treated with polylysine or silane to facilitate attachment of nucleic acid molecules. Silanization of glass surfaces for oligonucleotide applications has been described (see, Halliwell et al., *Anal. Chem.* 73:2476-2483, 2001). In some embodiments, the surface of the substrate to which nucleic acid molecules are attached bears chemically reactive groups, such as carboxyl, amino, hydroxyl and the like (e.g., Si—OH functionalities, such as are found on silica surfaces).

The surface of the substrate may be treated with radiation, or a protectant or reactant species over selected areas, and the unprotected areas are then coated with a hydrophobic agent to yield a chemically differentiated surface. Thus, some areas of the surface are available for attachment of nucleic acid molecules, while others are not. For example, a hydrophobic coating can be created by chemical deposition of tridecafluorotetrahydrooctyl triethoxysilane onto exposed oxide surrounding the protected areas. The protectant is removed, exposing the regions of the substrate to further modification and synthesis of nucleic acid molecules (see, Maskos & Southern, *Nucl. Acids Res.* 20:1679-1684, 1992). By way of example, a glass substrate can be coated with a hydrophobic material, such as 3-(1,1-dihydroperfluoroctyloxy) propyltriethoxysilane, which is ablated at desired loci to expose the underlying silicon dioxide glass, which is subsequently treated with hexaethylene glycol and sulfuric acid to form an hydroxyl group-bearing linker upon which chemical species can be synthesized (see, U.S. Pat. No. 5,474,796, to Brennan). The protectant and the hydrophobic coating can be applied in any desired pattern by, for example, a printing process using a rubber stamp, a silk-screening process, or a laser printer with a hydrophobic toner.

In some embodiments of the methods of the invention, linker molecules are attached to the substrate and the nucleic acid molecule is then synthesized at the end of the linker. Examples of useful linker molecules include, for example, silane, aryl acetylene, ethylene glycol, diamines, diacids, amino acids, peptide molecules including protease recognition sites, or combinations thereof. The linker molecules may be attached to the substrate via carbon-carbon bonds using, for example, (poly)trifluorochloroethylene surfaces, or, for example, by siloxane bonds to glass or silicon oxide surfaces. Methods of silanization of glass surfaces for oligonucleotide attachment are further described in Halliwell et al., *Anal. Chem.* 73:2476-2483, 2001.

The linker molecules may be attached, for example, in an ordered array, such as parts of head groups in a polymerized Langmuir Blodgett film, or as a self-assembling monomer (see, Silberzan et al., *Langmuir* 7:1647-1651, 1991). The linker molecules may be provided with a functional group to which is bound a protective group, such as a photolabile protecting group. In some embodiments, the linker contains a photocleavable spacer such as photocleavable spacer phosphoramidite monomers (available from Glen Research, 22825 Davis Drive, Sterling, Va. 20164) which can be synthesized on a silanized glass substrate with hydroxyl functionality. In some embodiments, the nucleic acid molecule is directly attached to a linker by an ester bond. By way of non-limiting example, a silane linker may be covalently attached to a silica surface of the substrate and the first nucleotide of the nucleic acid molecule is synthesized directly onto the hydroxyl group on the silane linker.

A population of nucleic acid molecules can be synthesized on a substrate by any art-recognized means including, for example, photolithography (see, Lipshutz et al., *Nat. Genet.* 21 (1 Suppl):20-24, 1999) and piezoelectric printing (see, Blanchard et al., *Biosensors and Bioelectronics* 11:687-690, 1996). In some embodiments, nucleic acid molecules are synthesized in a defined pattern on a solid substrate to form a high-density microarray. Techniques are known for producing arrays containing thousands of oligonucleotides comprising defined sequences at defined locations on a substrate (see e.g., Pease et al., *Proc. Nat'l. Acad. Sci.* 91:5022-5026, 1994; Lockhart et al., *Nature Biotechnol.* 14:1675-80, 1996; and Lipshutz et al., *Nat. Genet.* 21 (1 Suppl):20-4, 1999).

In some embodiments, predetermined nucleic acid sequences are synthesized on a substrate, to form a high density microarray, by means of an ink jet printing device for oligonucleotide synthesis, such as described by Blanchard in U.S. Pat. No. 6,028,189; Blanchard et al., *Biosensors and Bioelectrics* 11:687-690 (1996); Blanchard, *Synthetic DNA Arrays in Genetic Engineering*, Vol. 20, J. K. Setlow, Ed. Plenum Press, New York at pages 111-123, and U.S. Pat. No. 6,028,189 issued to Blanchard. The nucleic acid sequences in such microarrays are typically synthesized in arrays, for example on a glass slide, by serially depositing individual nucleotide bases in "microdroplets" of a high surface tension solvent such as propylene carbonate. The microdroplets have small volumes (e.g., 100 picoliters (pL) or less, or 50 pL or less) and are separated from each other on the microarray (e.g., by hydrophobic domains) to form surface tension wells which define the areas containing the array elements (i.e., the different populations of nucleic acid molecules). Microarrays manufactured by this ink-jet method are typically of high density, typically having a density of at least about 2,000 different nucleic acid molecules per 1 $cm^2$. The nucleic acid molecules may be covalently attached directly to the substrate, or to a linker attached to the substrate at either the 3' or 5' end of the polynucleotide. In the practice of the present invention, exemplary chain lengths of the synthesized nucleic acid molecules are in the range of about 20 to about 100 nucleotides in length, such as 50 to 100, 60 to 100, 70 to 100, 80 to 100, or 90 to 100 nucleotides in length. In some embodiments, the nucleic acid molecules are in the range of 80 to 100 nucleotides in length.

Exemplary ink jet printing devices suitable for oligonucleotide synthesis in the practice of the present invention contain microfabricated ink-jet pumps, or nozzles, which are used to deliver specified volumes of synthesis reagents to an array of surface tension wells (see, Kyser et al., *J. Appl. Photographic Eng.* 7:73-79, 1981). The pumps can be made, for example, by using etching techniques known to those skilled in the art to fabricate a shallow cavity and channels in silicon. A thin glass membrane is then anodically bonded to the silicon to seal the etched cavity, thus forming a small reservoir with narrow inlet and exit channels. When the inlet end of the pump is dipped in the reagent solution, capillary action draws the liquid into the cavity until it comes to the end of the exit channel. When an electrical pulse is applied to the piezoelectric element glued to the glass membrane it bows inward, ejecting a droplet out of the orifice at the end of the pump. For oligonucleotide synthesis in two dimensional arrays, pumps that deliver 100 pL droplets or less on demand at rates of several hundred Hertz (Hz) are applicable. However, the droplet volume or speed of the pump can vary depending on the need. For example, if a larger array is to be synthesized with the same surface area, then smaller droplets should be dispensed. Additionally, if synthesis time is to be decreased, then operation speed can be increased. Such parameters are known to those skilled in the art and can be adjusted according to the need (see e.g., U.S. Pat. No. 6,028,189, to Blanchard).

DNA synthesis can be carried out by any art-recognized chemistry, including phosphodiester, phosphotriester, phosphate triester or N-phosphonate and phosphoramidite chemistries (see e.g., Froehler et al., *Nucleic Acid Res* 14:5399-5407, 1986; McBride et al., *Tetrahedron Lett.* 24:246-248, 1983). Methods of oligonucleotide synthesis are well known in the art and generally involve coupling an activated phosphorous derivative on the 3' hydroxyl group of a nucleotide with the 5' hydroxyl group of the nucleic acid molecule (see e.g., Gait, *Oligonucleotide Synthesis: A Practical Approach*, IRL Press, 1984).

By way of example, a nucleotide having an activated phosphoramidite group at the 3' position, and a protected hydroxyl group at the 5' position, reacts with a nucleic acid molecule, attached to a substrate, having a thiol or hydroxyl group at its 5' position that is capable of forming a stable covalent bond with the phosphoramidite group at the 3' position. Each coupling step adds one nucleotide to the end of the attached nucleic acid molecule. After excess nucleotide monomer is washed away, a deprotection step reactivates the new end of the molecule for the next cycle (see, Blanchard et al., *Biosensors & Bioelectronics* 11 (6/7):687-690, 1996).

Suitable nucleotides useful in the synthesis of nucleic acid molecules of the invention include nucleotides that contain activated phosphorus-containing groups such as phosphodiester, phosphotriester, phosphate triester, H-phosphonate and phosphoramidite groups. In some embodiments, nucleic acid molecules can be synthesized using modified nucleotides, or nucleotide derivatives, such as for example, combinations of modified phosphodiester linkages such as phosphorothiate, phosphorodithioate and methylphosphonate, as well as nucleotides having modified bases such as inosine, 5'-nitroindole and 3' nitropyrrole. Additionally, it is possible to vary the charge on the phosphate backbone of the nucleic acid molecule, for example, by thiolation or methylation, or to use a peptide rather than a phosphate backbone. The making of such modifications is within the skill of one trained in the art.

Synthesis of nucleic acid molecules comprising RNA can similarly be accomplished using the present methods. A range of modifications can be introduced into the base, the sugar, or the phosphate portions of oligoribonucleotides, e.g., by preparation of appropriately protected phosphoramidite or H-phosphonate ribonucleoside monomers, and/or coupling such modified forms into oligoribonucleotides by solid-phase synthesis. Modified ribonucleoside analogues include, for example, 2'O-methyl, 2'-O-allyl, 2'-fluoro, 2'-amino phosphorothioate, 2'-O-Me methylphosphonate, 5'-O-Silyl-2'-O-ACE, 2'-O-TOM, alpha-ribose and 2'-5'-linked ribonucleoside analogs.

In some embodiments of the method of the invention, a population of nucleic acid molecules is synthesized to form a high-density microarray. A DNA microarray, or chip, is an array of nucleic acid molecules, such as synthetic oligonucleotides, disposed in a defined pattern onto defined areas of a solid support (see, Schena, *BioEssays* 18:427, 1996). The arrays are preferably reproducible, allowing multiple copies of a given array to be produced and easily compared with each other. Microarrays are typically made from materials that are stable under nucleic acid molecule hybridization conditions. In some embodiments, the nucleic acid molecules on the array are single-stranded DNA sequences. Exemplary microarrays and methods for their manufacture and use are set forth in T. R. Hughes et al., *Nature Biotechnology* 19: 342-347, April 2001, which publication is incorporated herein by reference.

Exemplary sizes (expressed as surface area) for microarrays are between 1 cm$^2$ and 25 cm$^2$, such as between 12 cm$^2$ and 13 cm$^2$ (by way of specific example, 3 cm$^2$). However, larger or smaller arrays are also contemplated.

In specific embodiments, DNA microarrays prepared in accordance with the present invention have a density of at least about 150 nucleic acid molecules per 1 cm$^2$ or higher. In some embodiments, DNA microarrays prepared in accordance with the present invention have at least 550, at least 1000, at least 1,500 or at least 2,000 nucleic acid molecules per 1 cm$^2$. In some embodiments, DNA microarrays prepared in accordance with the present invention are high density arrays, for example having a density of at least about 2,000 predetermined nucleic acid molecules per 1 cm$^2$ (e.g., at least 2,000, at least 5,000, at least 10,000 at least 15,000, at least 20,000, at least 25,000, at least 50,000, at least 55,000, at least 100,000, or at least 150,000 predetermined nucleic acid molecules per 1 cm$^2$).

In some embodiments, the array is a positionally addressable array in that each nucleic acid molecule of the array is localized to a known, defined area on the substrate such that the identity (i.e., the sequence) of each nucleic acid molecule can be determined from its position on the array (i.e., on the substrate surface). For example, a substrate may have at least from about 1,000 to about 30,000 separate defined areas. The size of each defined area on a substrate is chosen to allow for efficient cleavage of the synthesized nucleic acids. For example, in one embodiment, approximately 0.3 fmole of DNA is synthesized per defined area.

Typically in the practice of the methods of the invention, each of the synthesized nucleic acid molecules within a defined area has a nucleic acid sequence that is essentially identical to the nucleic acid sequence of every other synthesized nucleic acid molecule localized to the same defined area. In these embodiments, the nucleic acid sequence of the nucleic acid molecules in each defined area may be the same as, or different from, the nucleic acid sequence(s) of the nucleic acid molecules localized in one or more other defined areas on the substrate. Thus, nucleic acid molecules having the same nucleic acid sequence can be synthesized on numerous defined areas of a substrate, thereby providing a large number of nucleic acid molecules having the same nucleic acid sequence.

For example, in some embodiments in which each of the synthesized nucleic acid molecules within a defined area has a nucleic acid sequence that is essentially identical to the nucleic acid sequence of every other synthesized nucleic acid molecule localized to the same defined area, more than 50% of the defined areas on the substrate contain synthesized nucleic acid molecules that have a nucleic acid sequence that is different from the nucleic acid sequences of the nucleic acid molecules contained on the other defined areas of the substrate. In some embodiments, greater than 60%, or greater than 70%, or greater than 80%, or greater than 90%, or greater than 95%, or greater than 99%, or all, of the defined areas on the substrate contain nucleic acid molecules with a nucleic acid sequence that is different from the sequences of the nucleic acid molecules on the other defined areas of the substrate.

To facilitate amplification and cloning of the synthesized nucleic acid molecules into a vector, each synthesized nucleic acid molecule may include a 5' primer binding region, and a 3' primer binding region. In these embodiments, the portion of the nucleic acid molecule located between the 5' primer binding region and the 3' primer binding region is referred to as the target sequence. The target sequence may, for example, encode a portion of a protein that is to be expressed.

In some embodiments, synthesized nucleic acid molecules further comprise an RNA polymerase promoter site, such as T7 or SP6, to allow for subsequent, in vitro, transcription in order to create a library of RNA molecules derived from the synthesized nucleic acid molecules.

Typically, the 5' primer binding region and the 3' primer binding region of the synthesized nucleic acid molecules range in length from about 4 to about 30 nucleotides, and may include restriction enzyme cleavage sites. The nucleotide sequences of the 5' binding region and 3' primer binding region may be chosen to allow for efficient amplification and typically have an annealing temperature within about 20° C. of each other. Computer programs are useful in the design of primers with the required specificity and optimal amplification properties. See, e.g., Oligo version 5.0 (available from National Biosciences Inc., 3001 Harbor Lane, Suite 156, Plymouth, Minn. 55447-5434). The same 5' primer binding region and/or 3' primer binding region may be present in all of the synthesized nucleic acid molecules, or a particular 5' primer binding sequence or 3' primer binding sequence may be present in only a subpopulation of the synthesized nucleic acid molecules, thereby allowing for selective amplification of the subpopulation of the synthesized nucleic acid molecules.

Thus, the population of synthesized nucleic acid molecules may include a first sub-population of synthesized nucleic acid molecules and a second sub-population of synthesized nucleic acid molecules, wherein: (a) each synthesized nucleic acid molecule within the first sub-population of synthesized nucleic acid molecules includes a 5' primer binding region that is essentially identical to every other 5' primer binding region within the first sub-population of synthesized nucleic acid molecules, but that is different from every 5' primer binding region within the second sub-population of synthesized nucleic acid molecules; (b) each synthesized nucleic acid molecule within the second sub-population of synthesized nucleic acid molecules includes a 5' primer binding region that is essentially identical to every other 5' primer binding region within the second sub-population of synthesized nucleic acid molecules, but that is different from every 5' primer binding region within the first sub-population of synthesized nucleic acid molecules; and (c) the first sub-population of synthesized nucleic acid molecules and the second sub-population of synthesized nucleic acid molecules are localized to separate defined areas of the substrate.

Also, the population of synthesized nucleic acid molecules may include a first sub-population of synthesized nucleic acid molecules and a second sub-population of synthesized nucleic acid molecules, wherein: (a) each synthesized nucleic acid molecule within the first sub-population of synthesized nucleic acid molecules includes a 3' primer binding region that is essentially identical to every other 3' primer binding region within the first sub-population of synthesized nucleic acid molecules, but that is different from every 3' primer binding region within the second sub-population of synthesized nucleic acid molecules; (b) each synthesized nucleic acid molecule within the second sub-population of synthesized nucleic acid molecules includes a 3' primer binding region that is essentially identical to every other 3' primer binding region within the second sub-population of synthesized nucleic acid molecules, but that is different from every 3' primer binding region within the first sub-population of synthesized nucleic acid molecules; and (c) the first sub-population of synthesized nucleic acid molecules and the second sub-population of synthesized nucleic acid molecules are localized to separate defined areas of the substrate.

Target sequences of the synthesized nucleic acid molecules may encode, for example, a portion of a protein to be expressed. In some embodiments, the target sequence of each nucleic acid molecule localized to a particular defined area of the substrate is different from the target sequence of each nucleic acid molecule localized to different defined areas of the substrate. Thus, in some embodiments, each defined area on a substrate contains a different target sequence. In some embodiments, more than 50% of the defined areas on the substrate contain synthesized nucleic acid molecules that have a target sequence that is different from the target sequences of the nucleic acid molecules contained on the other defined areas of the substrate. In some embodiments, greater than 60%, or greater than 70%, or greater than 80%, or greater than 90%, or greater than 95%, or greater than 99%, or all, of the defined areas on the substrate contain nucleic acid molecules with a target sequence that is different from the sequence of all of the target sequences on separate defined areas of the substrate.

In some embodiments, the synthesized nucleic acid molecules additionally contain a target identifier sequence to facilitate selective amplification of a particular target sequence out of the population of synthesized nucleic acid molecules. Typically, the length of the target identifier sequence is from about 4 base pairs to about 8 base pairs. The target identifier sequence is located anywhere within the synthesized nucleic acid molecule, such as immediately adjacent to either the 5' end or the 3' end of the synthesized nucleic acid molecule. A target identifier sequence that consists of only four bases provides for 256 different unique nucleic acid sequences, and a target identifier sequence that consists of only eight bases provides for 65,536 different unique nucleic acid sequences. In some embodiments, each target identifier sequence is associated with a particular target sequence. In some embodiments, each target identifier sequence is associated with a predetermined sub-population of target sequence(s).

The synthesized nucleic acid molecules can be harvested from the substrate by any useful means. In some embodiments, the portion of the nucleic acid molecule that is directly attached to the substrate, or attached to a linker that is attached to the substrate, is attached to the substrate or linker by an ester bond which is susceptible to hydrolysis by exposure to a hydrolyzing agent, such as hydroxide ions, for example, an aqueous solution of sodium hydroxide or ammonium hydroxide. The entire substrate can be treated with hydrolyzing agent, or alternatively, a hydrolyzing agent can be applied to a portion of the substrate. For example, a silane linker can be cleaved by exposure of the silica surface to ammonium hydroxide, yielding various silicate salts and releasing the nucleic acid molecules with silane linker into solution. In some embodiments, ammonium hydroxide can be applied to the portion of a substrate that is covalently attached to the nucleic acid molecules, thereby releasing the nucleic acid molecules into solution (see, Scott and McLean, *Innovations and Perspectives in Solid Phase Synthesis*, 3$^{rd}$ International Symposium, 1994, Mayflower Worldwide, 115-124). The present inventors have observed that ammonium hydroxide can be used to harvest synthesized nucleic acid molecules from a substrate, even if the synthesized nucleic acid molecules are not attached to the substrate by a chemical bond that is cleavable using ammonium hydroxide. While not wishing to be bound by theory, the ammonium hydroxide may etch or scrape the substrate to release the synthesized nucleic acid molecules therefrom. In embodiments comprising a photocleavable linker, the linker can be cleaved by exposure to light of appropriate wavelength, such as for example, ultra violet light, to harvest the nucleic acid molecules from the substrate (see J. Olejnik and K. Rothschild, *Methods Enzymol* 291:135-154, 1998).

Once synthesized nucleic acid molecules are harvested they are cloned into vector molecules. Typically, harvested nucleic acid molecules are single stranded DNA molecules which may require second-strand synthesis to form double stranded DNA molecules prior to cloning into vector molecules. Second-strand synthesis may be achieved, for example, by first annealing a DNA oligonucleotide primer to a portion of each of the synthesized nucleic acid molecules (e.g., annealing a primer that hybridizes to a primer binding region). A DNA polymerizing enzyme, such as Taq polymerase or the Klenow fragment of *E. coli* DNA polymerase I, is then added to complete second-strand synthesis, resulting in double-stranded DNA molecules. Second strand synthesis can also occur, for example, during the first cycle of a series of amplification reactions (e.g., PCR reactions).

In some embodiments, a population of nucleic acid molecules are synthesized, on a substrate, that include complementary nucleic acid molecules which are annealed after harvesting to form double-stranded DNA molecules which are ready to be introduced into a vector. Thus, in some aspects of the methods of the invention for making populations of nucleic acid molecules, the population of synthesized nucleic acid molecules comprises a first sub-population of synthesized nucleic acid molecules and a second sub-population of synthesized nucleic acid molecules, wherein: (a) each member of the first sub-population of synthesized nucleic acid molecules is identical to substantially every other member of the first sub-population of synthesized nucleic acid molecules; (b) each member of the second sub-population of synthesized nucleic acid molecules is identical to substantially every other member of the second sub-population of synthesized nucleic acid molecules; (c) each member of the first sub-population of synthesized nucleic acid molecules is complementary to substantially all members of the second sub-population of synthesized nucleic acid molecules (e.g., each member of the first sub-population of synthesized nucleic acid molecules is complementary to at least 99% of the second sub-population of synthesized nucleic acid molecules); (d) the first sub-population of synthesized nucleic acid molecules is annealed to the second sub-population of synthesized nucleic acid molecules after the first and second sub-populations of synthesized nucleic acid molecules are harvested from the substrate, to produce a population of double stranded nucleic acid molecules; and (e) the population of double stranded nucleic acid molecules are cloned into a population of vector molecules. In this context, the phrase "identical to substantially every other member" means identical to 99%, or more, of the relevant sub-population of nucleic acid molecules.

In some embodiments, the harvested nucleic acid molecules are amplified prior to introduction into vector molecules. Amplification can be achieved using any method of nucleic acid molecule amplification, including, for example, polymerase chain reaction (PCR), ligase chain reaction (Wu and Wallace, *Genomics* 4:560-569, 1989; Landegren et al., *Science* 241:1077-1080, 1988), transcription amplification (Kwoh et al., *Proc. Nat'l. Acad. Sci.* 87:1874-1878, 1990), self-sustained sequenced replication (Guantelli et al, *Proc. Nat'l. Acad. Sci.* 87:1874-1878, 1987), and nucleic acid based sequence amplification (NASBA).

PCR amplification methods are well known in the art and are described, for example, in Innis et al., eds., 1990, *PCR*

*Protocols: A Guide to Methods and Applications*, Academic Press Inc. San Diego, Calif. An amplification reaction typically includes the DNA that is to be amplified, a thermostable DNA polymerase, two oligonucleotide primers, deoxynucleotide triphosphates (dNTPs), reaction buffer and magnesium. Typically a desirable number of thermal cycles is between 1 and 25. Methods for primer design and optimization of PCR conditions are well known in the art and can be found in standard molecular biology texts such as Ausubel et al., *Short Protocols in Molecular Biology*, Wiley, 1995; and Innis et al, *PCR Protocols*, Academic Press, 1990. Taq DNA polymerase generates single dA overhangs on the 3' ends of the PCR product, allowing for ease of cloning into vectors that contain "T" overhangs complementary to those on the PCR product, such as TA Cloning vectors (available from Invitrogen Corporation, 1600 Faraday Avenue, PO Box 6482, Carlsbad, Calif. 92008).

Any primers that are complementary to a portion of the nucleic acid molecules that are synthesized on the substrate can be used to prime the polymerase chain reaction. For example, in one embodiment, a primer hybridizes to the 5' primer binding region of the nucleic acid molecule to be amplified, and the same primer, or a different primer, hybridizes to the 3' primer binding region of the nucleic acid molecule to be amplified. In another representative embodiment, a primer hybridizes to the target identifier sequence of the nucleic acid molecule to be amplified, and a different primer hybridizes to the 3' primer binding region of the nucleic acid molecule to be amplified. The primer binding regions of the nucleic acid molecules to be amplified, and hence the corresponding complementary PCR primers, preferably range in length from about 4 to about 30 nucleotides. Computer programs are useful in the design of primers with the required specificity and optimal amplification properties (e.g., Oligo Version 5.0 (National Biosciences)). In some embodiments, the PCR primers may additionally contain recognition sites for restriction endonucleases, to facilitate insertion of the amplified DNA fragment into specific restriction enzyme sites in a vector. If restriction sites are to be added to the 5' end of the PCR primers, it is preferable to include a few (e.g., two or three) extra 5' bases to allow more efficient cleavage by the enzyme. In some embodiments, the PCR primers may also contain an RNA polymerase promoter site, such as T7 or SP6, to allow for subsequent in vitro transcription in order to create a library of RNA molecules derived from the nucleic acid molecules that were synthesized on the substrate.

PCR amplification products can be purified using any suitable means. For example, such means include gel electrophoresis, column chromatography, high pressure liquid chromatography (HPLC) or physical means such as mass spectroscopy.

In the practice of the invention, synthesized nucleic acid molecules are harvested from a substrate, and are then introduced into vector molecules to form a nucleic acid library. The term "vector" refers to a nucleic acid molecule, usually double-stranded DNA, which is designed to receive another nucleic acid molecule (usually called the insert nucleic acid molecule), such as a nucleic acid molecule synthesized in accordance with the present invention. The vector is typically used to transport the insert nucleic acid molecule into a suitable host cell, or can be used, for example, in an in vitro system capable of utilizing elements in the vector. A vector may contain the necessary elements that permit transcribing, and optionally translating, the insert nucleic acid molecule into an RNA molecule, and optionally a polypeptide. This type of vector is called an expression vector. The insert nucleic acid molecule can be any nucleic acid molecule. Once in the host cell, the vector may replicate independently of, or coincidental with (e.g., by genomic integration), the host chromosomal DNA, and several copies of the vector and its inserted nucleic acid molecule may be generated.

The vectors useful in the practice of the present invention can also include other regulatory sequences, such as promoters, translation leader sequences, introns, and polyadenylation signal sequences. "Promoter" refers to a DNA sequence involved in controlling the expression of a coding sequence or functional RNA. In general, a coding sequence is located within the molecule at a position 3' of the promoter sequence. The term "promoter" includes a minimal promoter that is a short DNA sequence comprised of a TATA-box and/or other sequences that serve to specify the site of transcription initiation, to which regulatory elements may be added for control of expression. Promoters may be derived in their entirety from a native gene, or be composed of different elements derived from different promoters found in nature, or even comprise synthetic DNA segments.

Examples of vectors suitable for use in the method of the invention include plasmids, phages, cosmids, phagemids, viruses (e.g., retroviruses, lentiviruses, parainfluenzavirus, herpesviruses, reoviruses, paramyxoviruses, and the like). Commonly, vectors contain selection markers, such as genes encoding drug resistance to tetracycline, neomycin, hygromycin, or puromycin, or other genes that permit selection of cells transduced with the desired DNA sequences, such as hypoxanthine guanine phosphoribosyl transferase (HPRT), dihydrofolate reductase (DHFR), or thymidine kinase (TK).

Examples of vectors that are functional in plants are binary plasmids derived from *Agrobacterium* plasmids. Such vectors are capable of genetically transforming plant cells. Briefly, these vectors typically contain left and right border sequences that are required for integration into the host (plant) chromosome. Typically, between these border sequences is the nucleic acid molecule (such as a cDNA) to be expressed under control of a promoter. In some embodiments, a selectable marker and a reporter gene are also included. The vector also may contain a bacterial origin of replication.

Methods for introducing DNA inserts into vectors are well known in the art (see Sambrook et al. (1989) *Molecular Cloning: A Laboratory Manual*, $2^{nd}$ ed., Cold Spring Harbor Press, Plainview, N.Y. (1989), and Ausubel et al., *Current Protocols in Molecular Biology* (Supplement 47), John Wiley & Sons, New York, 1999). Various methods can be used in the cloning process, such as for example, PCR products that have restriction enzyme sites incorporated within, either as a result of synthesis or as a consequence of PCR amplification utilizing primers containing such sites, can be digested and cloned into a plasmid vector with compatible ends. Alternatively, selective adaptors having recognition sites compatible with the expression vector of choice can be ligated to the ends of PCR products. Selective adaptors can be produced by well-known methods for the production of oligonucleotides (see Gait, *Oligonucleotide Synthesis: A Practical Approach*, IRL Press, 1984). Double stranded adaptors are typically produced one strand at a time and annealed prior to addition to the digested insert population. Adaptors can also be added to the ends of amplification primers. In addition, TA cloning vectors (Invitrogen) which contain 3' T overhangs can be used to clone PCR products that have been amplified using Taq polymerase and therefore have a corresponding 3' A overhang on the end of each PCR product.

The vectors containing the DNA inserts of interest may be transferred into a host cell by well-known methods, depending on the type of cellular host. For example, calcium chloride transfection is commonly utilized for prokaryotic cells, whereas calcium phosphate treatment, lipofection or electroporation are exemplary procedures that may be used for other cellular hosts. Other methods used to transform mammalian cells include the use of viral infection, polybrene, protoplast fusion, liposomes, cationic transfection procedures, and microinjection. Once the vector has been incorporated into an appropriate host, the host may be maintained under conditions suitable for high level expression of the nucleotide sequences, and expressed polypeptides collected and purified. Once purified, the polypeptides can be used, for example, in screening assays.

The overall quality of the nucleic acid molecule synthesis can be assessed at several stages during practice of the invention. For example, the quality of nucleic acid synthesis can be determined prior to harvesting the nucleic acid molecules from the substrate, using functional hybridization of a standard quality control template.

The overall quality of the synthesized nucleic acid molecules and the depth of library coverage can be determined, for example, by sequencing individual clones to determine the percent of nucleic acid molecules containing accurate and complete sequences as compared with the expected set of predetermined sequences. If it is determined that a subset of expected sequences are not present in the library, then the methods of the invention can be used to synthesize the missing sequences.

Figure 1:
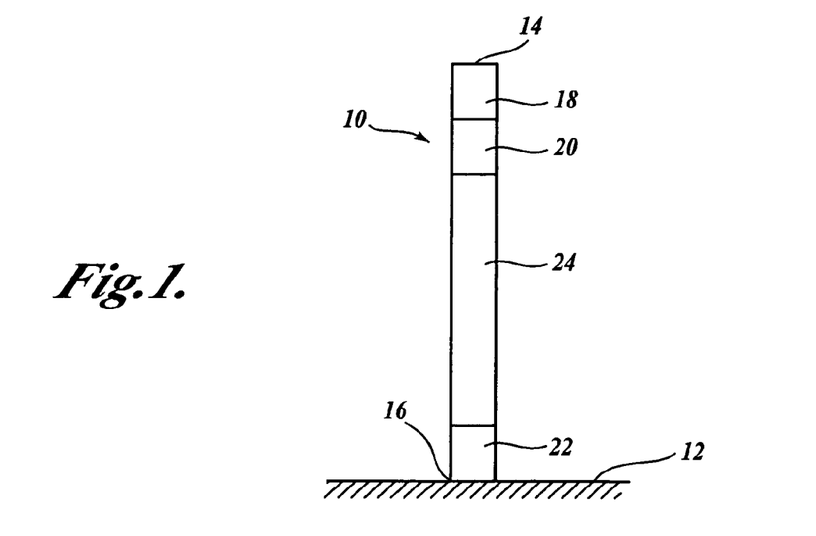
FIG. 1 shows a representative nucleic acid molecule synthesized on a substrate in accordance with the methods of the invention.

In accordance with the foregoing, and to facilitate understanding of the invention, FIG. 1 shows a representative nucleic acid molecule 10 synthesized on a substrate 12 in accordance with the present invention (although it will be understood that, in the practice of the invention, numerous nucleic acid molecules 10 are simultaneously synthesized on substrate 12). Nucleic acid molecule 10 includes a 5' end 14 and a 3' end 16 which is covalently attached to substrate 12. A target identifier sequence 18 is located immediately adjacent to 5' end 14, and between 5' end 14 and a 5' primer binding region 20. A 3' primer binding region 22 is located immediately adjacent to 3' end 16 of nucleic acid molecule 10. A target sequence 24 is located between 5' primer binding region 20 and 3' primer binding region 22.

Figure 2:
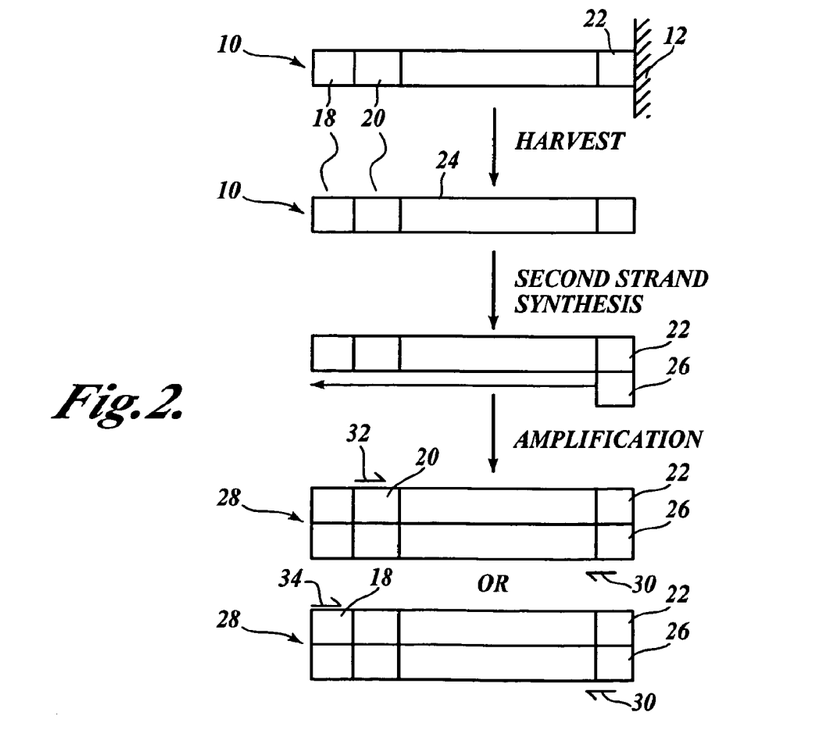
FIG. 2 shows a representative method for harvesting and amplifying nucleic acid molecules synthesized in accordance with the methods of the invention.

FIG. 2 shows a representative method for harvesting and amplifying nucleic acid molecule 10 from substrate 12 to yield a double stranded nucleic acid molecule that can be cloned into a vector (although it will be understood that, in the practice of the invention, numerous nucleic acid molecules 10 are simultaneously harvested and amplified). Thus, nucleic acid molecule 10 is harvested from substrate 12 (e.g., by exposure to ammonium hydroxide) and a complementary oligonucleotide primer 26 is hybridized to 3' primer binding region 22 to prime second strand synthesis that is catalyzed, for example, by the Klenow fragment of DNA polymerase I, thereby yielding a double stranded DNA molecule 28. Thereafter, double stranded DNA molecule 28 can be amplified, for example by a PCR reaction utilizing primers complementary to a single stranded portion of double stranded DNA molecule 28. For example, the combination of a primer 30 that hybridizes to the complement of 3' primer binding region 22, and a primer 32 that hybridizes to 5' primer binding region 20 can be used. Again by way of example, the combination of primer 30 that hybridizes to the complement of 3' primer binding region 22, and a primer 34 that hybridizes to target identifier sequence 18 can be used. Amplified double stranded DNA molecules 28 can be cloned into a vector molecule, for example by blunt end ligation, or by using restriction enzyme sites present in amplified double stranded DNA molecules 28.

The following examples merely illustrate the best mode now contemplated for practicing the invention, but should not be construed to limit the invention.

Example 1

This example describes the synthesis of oligonucleotide microarrays, useful in the practice of the invention, using ink-jet technology.

Preparation of Substrate:

Prior to oligonucleotide synthesis borosilicate glass wafers (3"×3"×0.004") were silanized with two silane species to yield hydroxyl functionality. The glass wafers were then washed for 3 hours with a 1.5% Alconox detergent (Alconox, Inc., New York, N.Y.), made in nanopure water, with sonication and heat. In order to increase substrate surface hydrophobicity, a solution was prepared in which N-decyltrichlorosilane (Gelest, Morrisville Pa.) was added under nitrogen to 11-trichlorosilyl-1-undecene (Gelest, Morrisville Pa.) which provides reactive functionality, in a 30:1 ratio to anhydrous m-xylene (Sigma Aldrich) for a final concentration of 0.02% (v/v). The washed glass wafers were reacted with the above solution under a positive flow of argon for 5 hours at 80° C. The glass wafers were then rinsed, dried, and placed in borane tetrahydrofuran for 2 hours at room temperature. Finally, the wafers were placed in 0.1M $NaOH/H_2O_2$ for 10 minutes to confer the anti-markonikov addition of the hydroxyl group to the undecenyl silane.

Synthesis of a Photocleavable (PC) Spacer:

All reaction steps and reagent preparations were performed under nitrogen in a PLAS-LABS 830-ABC glove box. Photocleavable ("PC") spacer phosphoramidite monomers (Glen Research) were synthesized on a silanized glass wafer with hydroxyl functionality. Anhydrous acetonitrile (1 mL: Fisher Scientific) was added via syringe injection to 100 μmoles of freeze-dried PC spacer phosphoramidite to yield a 0.1M solution. 62 mL of anhydrous acetonitrile were added to 2 grams of freeze-dried 5-ethylthiol-1H-tetrazole (Glen Research) to yield a 0.25M solution for phosphoramidite activation. The solutions were vortexed briefly and allowed to equilibrate at room temperature for 30 minutes. The tetrazole solution (1 mL) was then transferred by syringe to the PC spacer solution and the mixture was vortexed for 10 seconds. Two silanized glass wafers were placed reactive side up, and 2 mL of the activated PC/tetrazole solution was added to the surface of the first glass wafer. The second wafer was placed sandwich-like on the first, allowing the fluid surface tension to distribute uniformly between the surfaces. The wafers were incubated at room temperature for 2 minutes, separated, placed in a Teflon™ rack and immersed in a bath of acetonitrile. The rack was agitated in the bath for 2 minutes to ensure complete rinsing of excess PC spacer and dried by centrifugation.

Synthesis of Nucleic Acid Molecules:

In situ oligonucleotide synthesis was carried out using the phosphotriester method. Hydroxyl functionalized 3"×3"×0.004" substrates were aligned robotically prior to each monomer synthesis via calibrated fiducial marks. Each substrate was then passed over the printhead apparatus wherein the piezo actuated ink-jet nozzles deposited 160 pL of a 0.3M phosphoramidite monomer (dA, dC, dG or dT, Proligo, CO) in anhydrous propylene carbonate (Sigma Aldrich) and 160 pL of 1.2 M 5-ethylthio-1H-tetrazole (Glen Research, VA) in anhydrous propylene carbonate. Each resultant deposition was therefore a mixture of a particular phosphoramidite (e.g., dA, dC, dG or dT) with the activator solution at a defined area of the substrate predetermined according to the design of the microarray. The substrate with the deposited monolayer was then placed robotically into a flowcell chamber where excess activated phosphoramidite was rinsed off with anhydrous acetonitrile (Fisher Scientific, CA). An oxidizer solution containing 4.3 g/L iodine in THF/H$_2$O/pyridine (90:9:1) was then incubated with the substrate for 30 seconds to yield the stable pentavalent phosphotriester. Removal of the oxidizer solution was followed by an additional rinse of anhydrous acetonitrile. Acid catalyzed deprotection of the 5' hydroxyl was then carried out with a one minute reaction with 3% dichloroacetic acid solution in m-xylene (w/v) to remove the dimethoxytrityl group, yielding an active 5' hydroxyl for the next phosphoramidite coupling step. After a final acetonitrile rinse, the substrate was transferred by robot back to the printhead chamber for calibration and subsequent coupling of the next monomer layer. This process was repeated n−1 times, where n is the length of the oligonucleotide probe. Final deprotection of the synthesized oligonucleotide was carried out with 99% ethanolamine (Fisher Scientific, CA), followed by a twenty minute incubation at room temperature, a rinse with deionized water, and centrifugation.

Harvesting Synthesized Nucleic Acid Molecules:

two methods were used to harvest the synthesized nucleic acid molecules:

Method 1: Cleavage of a Photocleavable Spacer.

Two 2 mL poly-vinyl chloride microarray hybridization chambers were laid face up and 1 mL of 25 mM Tris buffer solution (pH 7.4) was added to the center of each chamber. Each microarray was eased onto the open chamber, nucleic acid molecule side down, allowing the buffer to spread uniformly between the silanized glass and PVC hydrophobic surfaces. A UV lamp with a 300 nm cut off filter (VWR, 1310 Goshen Parkway, West Chester, Pa. 19380) was used to directly irradiate the microarray for 30 minutes. The microarray was lifted slowly with a stainless steel dentist pick, while the 1 mL solution of cleaved nucleic acid molecules and buffer was withdrawn by pipette from the chamber well. The solution was then transferred to a 1.5 mL microcentrifuge tube and dried by vacuum centrifugation at 50° C. overnight.

Method 2: Cleavage Using Ammonium Hydroxide.

Two 2 mL poly-vinyl chloride microarray hybridization chambers were laid face up in a laboratory fume hood. 1 mL of concentrated 35% NH$_4$OH solution (Fisher Scientific) was added to the center of each chamber. Each microarray was eased onto the open chamber, nucleic acid molecule side down, allowing the buffer surface tension to spread between the silanized glass and the PVC (hybridization chamber) hydrophobic surfaces. Nucleic acid molecules were then cleaved using either a 2 hour room temperature incubation, or a 1 hour incubation with sonication. After cleavage, the microarray was lifted slowly with a stainless steel dentist pick, while the 1 mL of cleaved nucleic acid molecules and buffer was withdrawn by pipette from the chamber well. The solution was then transferred to a 1.5 mL microcentrifuge tube and dried by vacuum centrifugation at about 50° C. overnight.

PCR Amplification of Harvested Nucleic Acid Molecules:

Dried material containing nucleic acid molecules cleaved from each microarray was resuspended in 250 µL of RNase/DNase-free H$_2$O. PCR reactions were set up using 0.1 to 10.0 µL of the harvested material. Each PCR reaction contained 50 µL of 1× PCR buffer minus Mg (Invitrogen, Carlsbad, Calif.), 9% sucrose, 1.5 mM MgCl$_2$, 1 ng/µL forward and reverse primers, 125 µM dNTPs, and 0.05 U/µL Taq polymerase. Thermocycler conditions varied depending upon the length of the nucleic acid molecules and the melting temperature of the primers. A typical amplification was carried out for 10 to 40 cycles of 94° C. for 30 seconds (sec), annealing at appropriate temp for 30 sec, and extension at 72° C. for 90 sec. In preparation for cloning into Topo/TA cloning vectors (Invitrogen, Carlsbad Calif.), Taq polymerase was utilized in the PCR reaction and multiple cycle steps were followed up with a single 10 min extension at 72° C.

Purification of PCR Products:

PCR products were purified prior to cloning either by agarose gel purification using the QIAquick gel extraction protocol, or by column purification using the QIAquick PCR purification protocol (QIAgen).

Example 2

This example describes the synthesis of a population of nucleic acid molecules (called 59 mers) on a substrate, wherein each nucleic acid molecule has a chain length of 59 nucleotides.

Preparation of the Microarray:

A microarray was made that contained 110 randomly chosen, unique, 59 mer sequences, each represented 220 times on the array (in order to produce enough nucleic acid molecules for multiple experiments). The microarray was synthesized as described in Example 1.

Cleavage and PCR of Nucleic Acid Molecules:

Cleavage was carried out using either the photocleavage method or the ammonium hydroxide method described in Example 1. Products from each method were pooled and amplified by PCR as described in Example 1.

Results:

Using the ammonium hydroxide cleaved material, 100% (5/5) of the clones analyzed were full length (59 nucleotides) independent clones and correctly matched one of the predetermined sequences from the array.

Example 3

This example describes the synthesis of a population of nucleic acid molecules (called 96 mers) on a substrate, wherein each nucleic acid molecule has a chain length of 96 nucleotides.

Preparation of the Microarray:

Microarrays were made containing 96 mer nucleic acid molecules present either once per array or present at variable representation (ranging from 2 times to 1024 times) and printed as described in Example 1.

Cleavage and PCR of Nucleic Acid Molecules:

Cleavage was carried out using either the photocleavage method or the ammonium hydroxide method described in Example 1. Products from each method were pooled and amplified by PCR and cloned as described in Example 1.

Results:

Using the ammonium hydroxide method described in Example 1, an average of 63% of the clones contained full length inserts (96 nucleotides) and correctly matched sequences in the printed array.

The results above demonstrate that it is possible to obtain high fidelity synthesis of nucleic acid molecules of lengths up to at least 96 nucleotides. This is surprising because synthetic oligonucleotides of lengths longer than about 50 nucleotides typically contain a mixture of truncated and full length products. It was previously thought that the presence of truncated products would likely dominate any subsequent amplification steps and thereby decrease the efficiency of obtaining a library containing full length inserts of greater than 50 nucleotides. Therefore, the ability to synthesize nucleic acid molecules greater than 50 nucleotides with high fidelity using ink jet technology allows for the rapid design and construction of nucleic acid libraries.

Example 4

This example describes the use of microarray synthesis and amplification to generate a population of nucleic acid molecules that are ready to be introduced into vector molecules.

Preparation of the Microarray:

A microarray is designed to contain predetermined nucleic acid molecules that contain a common 5' primer binding region and a common 3' primer binding region. The nucleic acid molecules are designed to contain an additional 4 to 8 base pair target identifier sequence adjacent to the 5' or 3' end of the molecule to allow for target specific amplification. The microarray is synthesized as described in Example 1.

Harvesting Synthesized Nucleic Acid Molecules:

The population of synthesized nucleic acid molecules is harvested from the microarray in 1 mL of ammonium hydroxide solution, as described in Example 1, method 2.

PCR of Nucleic Acid Molecules:

The dried material is resuspended in 250 µL of RNase/DNase-free $H_2O$, and this suspension is used as a template for amplification. PCR reactions are set up using from 1 µL to 10 µL of the suspension with PCR primers specific for the 5' and 3' primer binding regions of the synthesized nucleic acid molecules. Typical thermocycler conditions are 94° C. for 5 minutes, 35 cycles at 94° C. for 30 seconds, 57° C. for 30 seconds, 72° C. for 1.5 minutes followed by 1 cycle at 72° C. for 10 minutes. PCR products are then purified either by using gel purification methods, such as the Qiagen Qiaquick Gel Extraction method, or by column purification, such as by using a Qiagen PCR purification kit.

Introduction of PCR Products into a Cloning Vector:

Depending upon the design of the nucleic acid molecules, and the method of amplification, the PCR products are cloned in one of the following ways:

Blunt-end cloning is achieved by cleaving the vector at a restriction enzyme site that leaves blunt ends, and combining the PCR products with the vector, ligating, transforming and screening for clones.

TA cloning is achieved by utilizing Taq DNA polymerase in the PCR reaction which generates single dA overhangs on the 3' ends of the PCR product, allowing for ease of cloning into vectors that contain "T" overhangs complementary to those on the PCR products, such as TA Cloning vectors (available from Invitrogen Corporation, 1600 Faraday Avenue PO Box 6482, Carlsbad, Calif.).

Restriction enzyme cloning is achieved by either appropriately designing the synthesized nucleic acid molecules to include unique restriction enzyme sites flanking the 5' and 3' regions of the target sequence to be cloned which are contained in the PCR products, or alternatively, by using PCR primers which contain recognition sites for restriction enzymes. The purified PCR products are then digested with the appropriate restriction enzyme(s) and ligated to a vector.

Screening Clones for Inserts:

Once clones are obtained, they can be screened by DNA sequencing, microarray analysis, or colony hybridization (e.g., pooling a population of individual colonies that are representative of the whole library, excising the cloned inserts from the pooled clones, labeling the excised inserts and using the labeled inserts to probe a microarray that contains the same sequences as, or is diagnostic of the sequences represented on, the microarray used to make the library; the number of hybridizing areas on the array provides a measure of how many different, synthesized, nucleic acid molecules are represented in the library). The length of synthesized nucleic acid molecule and the number of defined areas on the microarray representing each sequence will help to determine the appropriate number of clones to screen to assess the complexity and sequence representation of the synthesized population.

Supplementation of the Library:

The optional inclusion of a target identifier sequence in the design of the nucleic acid molecule allows for the supplementation of under represented clones into the library to increase its complexity. If it is determined after screening that particular target sequences are under-represented in the cloned population, the target identifier sequence can be used to selectively amplify a particular sequence or group of sequences through the use of a PCR primer specific to the identifier sequence to amplify a particular synthesized nucleic acid molecule. The subpopulation of sequences amplified is then cloned separately as previously described, the clones recovered, and then mixed back into the library.

Example 5

This example describes the use of microarray synthesis to directly generate a population of nucleic acid molecules that are ready to be introduced into vector molecules.

Preparation of the Microarray:

A microarray is designed to contain a set of predetermined nucleic acid molecules that are complementary to another set of predetermined nucleic acid molecules such that after harvest, the synthesized molecules will anneal to form double stranded molecules. The design of nucleic acid molecules to be used in this approach does not require primer binding regions. In order to utilize this approach, each nucleic acid molecule is synthesized in sufficient quantity to allow for ligation into a vector. Typically, the complementary strands are synthesized in a 1:1 ratio. The microarray can be synthesized as described in Example 1.

Harvesting Synthesized Nucleic Acid Molecules:

The population of synthesized nucleic acid molecules is harvested from the microarray in 1 mL of ammonium hydroxide solution, as described in Example 1, method 2.

Annealing Harvested Nucleic Acid Molecules and Ligation:

After being dried, the material is resuspended and annealed. For example, the resuspended material is heated to 95° C. for about 2 minutes, then slowly cooled over a period of several hours to room temperature (typically in the range of 22° C. to 25° C.). Annealing is conducted, for example, in TE buffer (10 mM Tris-HCL, pH 8.0, 1 mM EDTA) in a volume of 50 µL to 100 µL. The annealed material is then added to the prepared vector in a 2 µL reaction with a 1:1 ratio of insert to vector.

Introduction of Annealed Products into a Cloning Vector:

Depending on the design of the nucleic acid molecules, the cloning can be accomplished in the following ways:

The nucleic acid molecules are designed such that annealing results in 5' or 3' overhangs that are compatible with the overhangs resulting from digestion of a vector with particular restriction enzymes. In this case, the annealed nucleic acids are ligated directly into digested vectors.

Alternatively, restriction enzyme cloning can be achieved by appropriately designing the synthesized nucleic acid molecules to include unique restriction enzyme sites flanking the 5' and 3' regions of the target sequence to be cloned. The annealed double-stranded nucleic acid molecules are then digested with the appropriate restriction enzyme(s) and ligated to a vector digested with a compatible enzyme. Clones can be screened for inserts as described in Example 4.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for making a population of nucleic acid molecules, the method comprising:
    (a) harvesting a population of synthesized single-stranded nucleic acid molecules that are covalently attached to a microarray, wherein each of the synthesized nucleic acid molecules consists of a predetermined nucleic acid sequence consisting of:
        (i) a 5' primer binding region,
        (ii) a 3' primer binding region,
        (iii) one of a number of different target sequences located between the 5' and 3' primer binding regions, and additionally,
        (iv) one of a number of unique target identifier sequences,
    wherein the target identifier sequence is not comprised within the target sequence or primer binding regions, and
    wherein each unique target identifier sequence is associated with only one particular target sequence; and
    (b) amplifying the population of synthesized single-stranded nucleic acid molecules harvested in step (a) to generate a population of double-stranded DNA molecules.

2. The method of claim 1, wherein the synthesized nucleic acid molecules are covalently attached to the microarray via a linker.

3. The method of claim 1, wherein the synthesized nucleic acid molecules have an average length of from about 20 nucleotides to about 100 nucleotides.

4. The method of claim 1, wherein the microarray comprises a positionably addressable microarray.

5. The method of claim 1, wherein the microarray comprises from about 1,000 to about 30,000 defined areas.

6. The method of claim 1, wherein the harvesting comprises use of a hydrolyzing agent.

7. The method of claim 6, wherein the hydrolyzing agent comprises ammonium hydroxide.

8. The method of claim 1, wherein the harvesting comprises cleavage of a photocleavable linker.

9. The method of claim 1, wherein the target sequences comprise a nucleic acid library.

10. The method of claim 1, wherein the unique target identifier sequence has a length of from about 4 nucleotides to about 8 nucleotides.

11. The method of claim 10, wherein the unique target identifier sequence is 4 nucleotides long and has a sequence that is selected from the group consisting of the 256 nucleotide sequences that can be constructed from a 4 nucleotide sequence.

12. The method of claim 10, wherein the unique target identifier sequence is 8 nucleotides long and has a sequence that is selected from the group consisting of the 65,536 nucleotide sequences that can be constructed from an 8 nucleotide sequence.

13. The method of claim 1, wherein amplifying comprises a method selected from the group consisting of: polymerase chain reaction (PCR), ligase chain reaction, transcription amplification, self-sustained sequence replication, and nucleic acid based sequence amplification (NASBA).

14. The method of claim 1, wherein both the 5' primer binding region and the 3' primer binding region have a length of from about 4 nucleotides to about 30 nucleotides.

15. The method of claim 1, wherein the sequence of the 5' primer binding region is the same in each of said synthesized nucleic acid molecules.

16. The method of claim 1, wherein the sequence of the 3' primer binding region is the same in each of said synthesized nucleic acid molecules.

17. The method of claim 1, wherein the sequence of both the 3' primer binding region and the 5' primer binding region is the same in each of said synthesized nucleic acid molecules.

18. The method of claim 1, wherein the 5' primer binding region is located within the unique target identifier sequence.

19. The method of claim 1, wherein the 3' primer binding region is located within the unique target identifier sequence.

20. The method of claim 1, wherein only synthesized nucleic acid molecules having one or more specific target identifier sequences are amplified.

21. The method of claim 1, wherein the 3' primer binding region comprises a restriction endonuclease recognition site.

22. The method of claim 1, wherein the 5' primer binding region comprises a restriction endonuclease recognition site.

23. The method of claim 1, wherein each of said synthesized nucleic acid molecules further comprises an RNA polymerase promoter.

24. A method for making a population of nucleic acid molecules, the method comprising:
    (a) harvesting a population of synthesized single-stranded nucleic acid molecules that are covalently attached to a microarray, wherein each of the synthesized nucleic acid molecules consists of a predetermined nucleic acid sequence consisting of:
        (i) a 5' primer binding region,
        (ii) a 3' primer binding region,
        (iii) one of a number of different target sequences located between the 5' and 3' primer binding regions, and additionally,
        (iv) one of a number of unique target identifier sequences,
    wherein the target identifier sequence is not comprised within the target sequence or primer binding regions, and
    wherein each unique target identifier sequence is associated with a particular predetermined sub-population of target sequences; and
    (b) amplifying the population of synthesized single-stranded nucleic acid molecules harvested in step (a) to generate a population of double-stranded DNA molecules.

* * * * *